April 9, 1946. B. W. SILL Plant Pat. 679
ANEMONE-FLOWERED ECHINACEA PLANT
Filed Sept. 20, 1944
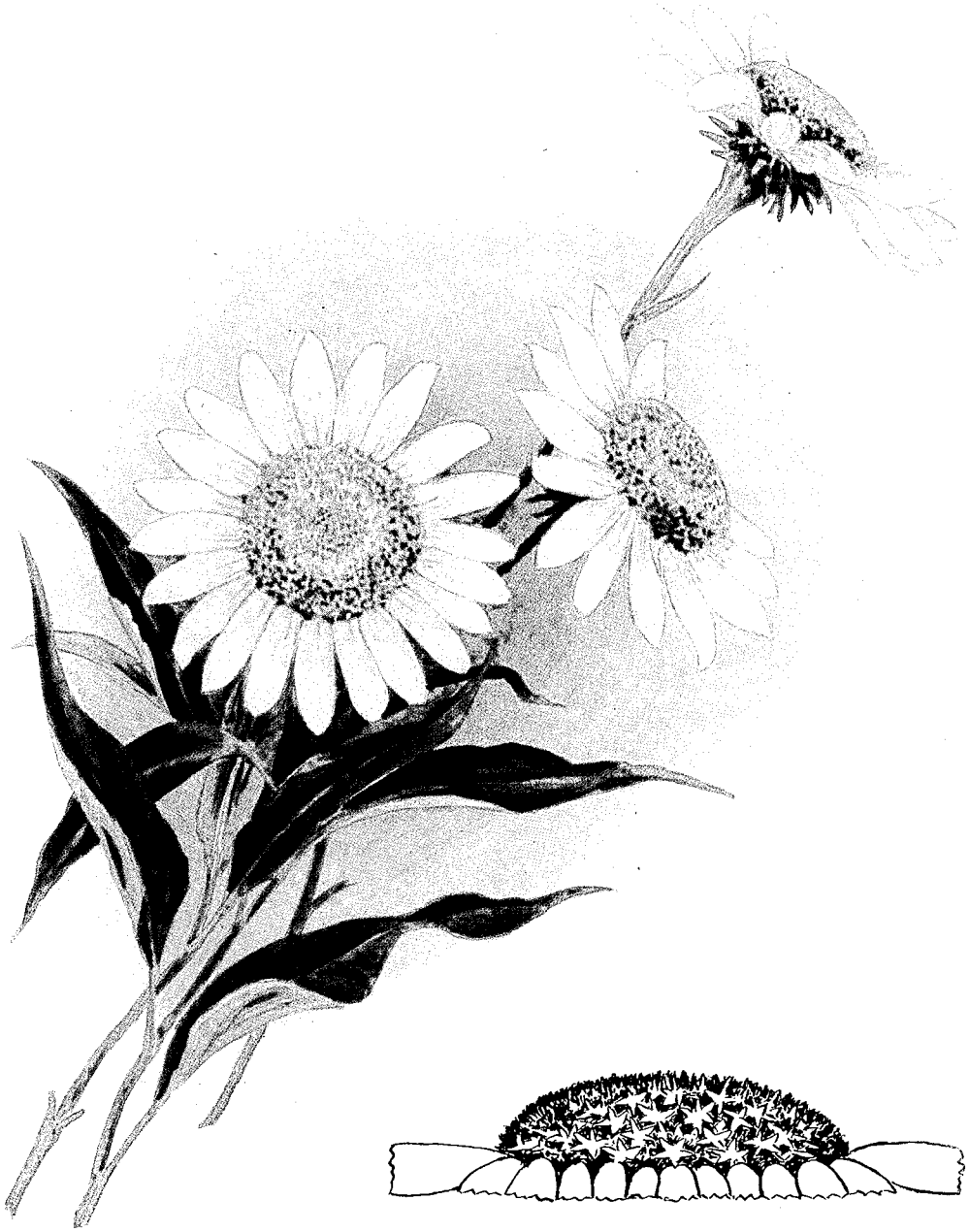
WITNESS
Addison E. Avery
INVENTOR,
BENJAMIN W. SILL, BY
Rummler Rummler & Davis,
his ATTORNEYS.

Patented Apr. 9, 1946

Plant Pat. 679

UNITED STATES PATENT OFFICE

679

ANEMONE-FLOWERED ECHINACEA PLANT

Benjamin William Sill, Atlanta, Ga.

Application September 20, 1944, Serial No. 554,891

1 Claim. (Cl. 47—60)

My present discovery relates to a new and distinct variety of Echinacea plant, being an offspring of the well-known variety *Echinacea purpurea*. Its novelty consists in a new combination of desirable features contributing to the beauty of color and conformation of the bloom.

The precursor of this new variety was a seedling, found in my greenhouse about the year 1935, which produced flowers whose ray petals stood out more nearly horizontal than those of the parent variety. Seeds from this seedling were saved and the following year some of the new plants were found to have improved in form and color. By repeated selection each year, one plant was found of the present form which will come true only by asexual propagation. These characteristics have been maintained by asexual propagation in quantity production.

The primary object in carrying out this invention was to improve the form and appearance of the flower; to establish the peculiar intense crimson color of the ray petals; to increase the number of such petals on each flower; and to develop the anemone-like floret petalage in place of the quills on the cone of the parent variety.

The accompanying illustration shows in full color typical branches of fully opened blossoms and a pen-and-ink sketch of the cone showing its substantially flat top with anemone-like florets.

This new variety in plant structure is outstandingly dissimiliar to the well-known *Echinacea purpurea* because of its more decorative appearance; its substantially flat center composed of dense clusters of star-shaped crimson colored individual florets, each having five petals fashioned into a tube with a star-shaped crown at the top, these forming the outer whorl mass which grades into an inner whorl group of scarcely opened florets forming pin-points of reddish-orange color. This formation of the cone gives it its anemone effect and greatly enhances the beauty of the flower as a whole.

Another important distinction is the horizontal attachment of its ray petals to the disk of the flower. This characteristic gives the flower a wide-awake healthy appearance in comparison with the drooping effect of the parent plant. The color of my new bloom is more intense, it has considerably more petals, it has a delicate fragrance, and is a splendid keeper as a cutflower.

On the other hand, the high disk of egg-shape and the downward angle at which the rays are pointed are common features of the ordinary Echinacea. The normal Echinacea is coarser looking in every way than my improved plant and flower.

The following is a detailed description of the new variety:

Parentage: Seedling. *Seed parent.—Echinacea purpurea.*

*Flower*

Blooming habit: Recurrent.

Bloom:

*Size.*—3 to 4 inches in diameter.
*Form.*—Daisy with quilled disk.
*Borne.*—Singly.
*Stems.*—Stout, erect.
*Petalage.*—Approximately 30.
*Discoloration.*—None.
*Texture.*—Firm.
*Affected by wet or hot weather.*—No.
*Fragrance.*—Pleasing and delicate.
*Disease resistance.*—Very good.
*Lasting quality.*—On plant—very good; as cut flower—very good.

*Plant*

Form: Bush; symmetrical.

*Height.*—2 to 3 feet.
*Texture.*—Of leaves—stiff, hispid; shape—ovate lanceolate.

The color designations according to "A Dictionary of Color of Maerz and Paul" are as follows:

| Section | Plate | Letter | No. |
|---|---|---|---|
| Main petal color at outer edge | 51 | J | 5 |
| Shading in darker tone at center | 51 | K | 7 |
| Main color of star-like florets forming cone | 4 | J | 6 |
| Florets near center of cone | 10 | L | 7 |
| Pin-points in center of cone | 3 | L | 5 |
| Main leaf color | 24 | L | 2 |
| Lower section of stems | 14 | L | 7 |

This new variety of Echinacea is easily distinguishable from all other varieties by its unusual coloring, desirable shape, and fullness of bloom, which are commercially advantageous characteristics.

Having thus disclosed my invention, I claim:

A new and useful variety of Echinacea plant with features in combination substantially as shown and described, characterized particularly by the horizontal disposition of the ray petals to its substantially flat compact floreted disk; the distinctive coloration of the flowers; its stout erect stems; its great resistance to disease; its excellent lasting qualities; and pleasing fragrance.

BENJAMIN WILLIAM SILL.